United States Patent
Federici et al.

(10) Patent No.: US 8,946,632 B2
(45) Date of Patent: Feb. 3, 2015

(54) SYSTEM AND METHOD FOR TERAHERTZ 2D INTERFEROMETRIC AND SYNTHETIC APERTURE IMAGING WITH AN INCOHERENT SOURCE

(75) Inventors: John Francis Federici, Westfield, NJ (US); Dale Gary, Berkeley Heights, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 325 days.

(21) Appl. No.: 12/943,506

(22) Filed: Nov. 10, 2010

(65) Prior Publication Data

US 2012/0153148 A1    Jun. 21, 2012

Related U.S. Application Data

(60) Provisional application No. 61/259,907, filed on Nov. 10, 2009.

(51) Int. Cl.
*H01L 27/146* (2006.01)
*G01N 21/3581* (2014.01)

(52) U.S. Cl.
CPC .......... *G01N 21/3581* (2013.01); *H01L 27/146* (2013.01)
USPC ........................................ 250/332

(58) Field of Classification Search
CPC ...................................................... H01L 27/146
USPC .................................. 250/332, 341.8, 338.1
See application file for complete search history.

(56) References Cited

U.S. PATENT DOCUMENTS

| | | | | |
|---|---|---|---|---|
| 6,144,679 A | * | 11/2000 | Herman et al. | 372/21 |
| 8,138,477 B2 | * | 3/2012 | Gregory | 250/341.1 |
| 2005/0156110 A1 | * | 7/2005 | Crawely | 250/338.1 |
| 2006/0214107 A1 | * | 9/2006 | Mueller | 250/341.8 |
| 2007/0257194 A1 | * | 11/2007 | Mueller | 250/341.8 |

* cited by examiner

*Primary Examiner* — David Porta
*Assistant Examiner* — Faye Boosalis
(74) *Attorney, Agent, or Firm* — Timothy X. Gibson, Esq.; Gibson & Dernier LLP

(57) ABSTRACT

An interferometric and synthetic aperture THz incoherent imaging system is provided, in which a high-power electronic source such as a 0.094 THz Gunn Oscillator is integrated with a continuous-wave (CW) terahertz detection system in order to achieve a high signal-to-noise ratio. THz imaging of a point source located 10 m away from the detector array is presented. A 2-D THz reflective image is reconstructed with only four detectors using rotational synthesis.

21 Claims, 8 Drawing Sheets

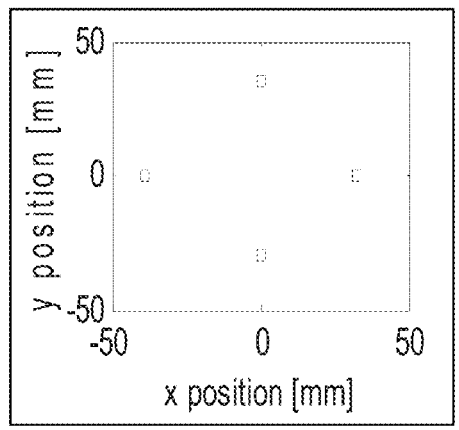
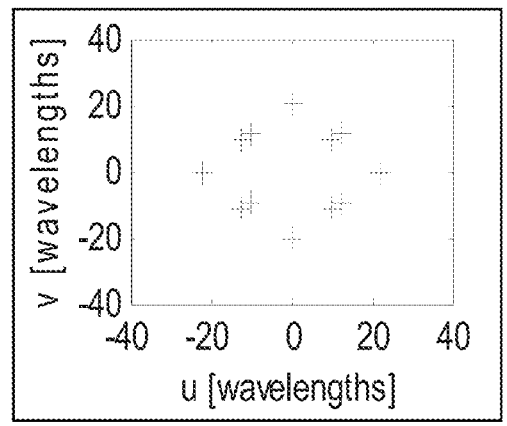
FIG. 1A
FIG. 1B
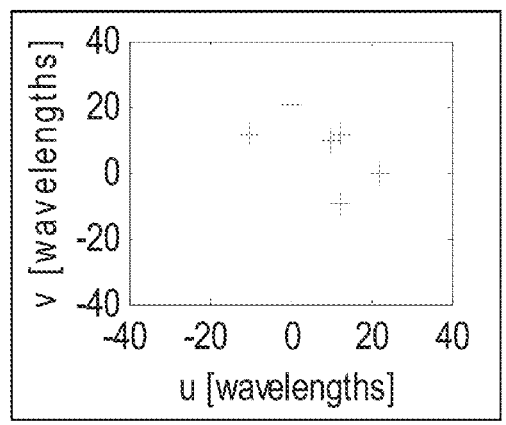
FIG. 1C

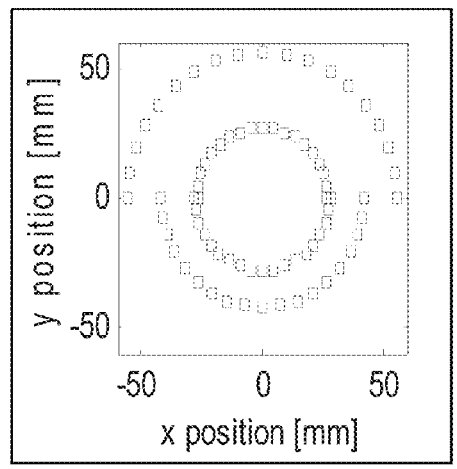 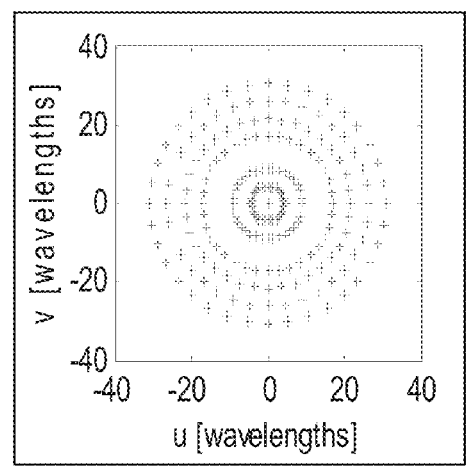
FIG. 3A  FIG. 3B
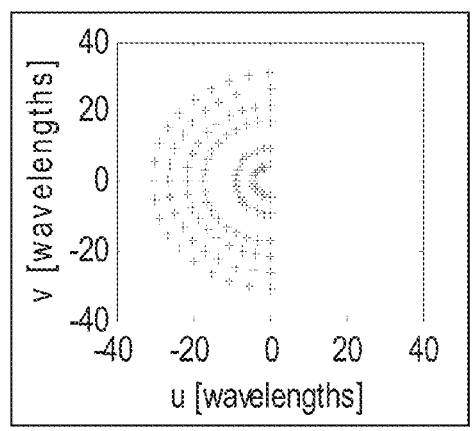
FIG. 3C

SYSTEM AND METHOD FOR TERAHERTZ 2D INTERFEROMETRIC AND SYNTHETIC APERTURE IMAGING WITH AN INCOHERENT SOURCE

CROSS-REFERENCE TO RELATED APPLICATIONS

This application claims the benefit of U.S. Provisional Patent Application No. 61/259,907 filed Nov. 10, 2009, the entirety of which is incorporated herein by reference.

GOVERNMENT RIGHTS

The research leading to the present invention was supported in part by the U.S. Department of the Army through contracts (DAAE30-03-D-1015-33; DAAE30-03-D-1015-22). Accordingly, the United States Government may have certain rights in the invention.

BACKGROUND

Recently, Terahertz (Thz) imaging has attracted more and more attention due to its applications to security screening, medical image, and stand-off detection of explosives. Federici et al., Semiconductor Science Technology 20, 266 (2005); Federici et al., "Counter-Terrorism Detection Techniques of Explosives", Jehuda Yinon, ed. (Elsevier, 2007). Various techniques for THz imaging have been reviewed by Chan et al., "Imaging with terahertz radiation," Rep. Prog. Phys. 70, 1325-1379 (2007). The most widespread THz imaging method used THz pulsed time-domain spectroscopy (THz TDS). Hu and Nuss, "Imaging with terahertz waves", Opt. Lett. 20, 1716 (1995). Using this method, 2-D images are acquired pixel-by-pixel. Two-dimensional electro-optic imaging using CW radiation has been reported. Wu et al., "Two-dimensional electro-optic imaging of THz beams," Appl. Phys. Lett. 69, 1026-1028. For this imaging method, the THz radiation is generated by the beating or mixing of two near-infrared laser sources in a THz photomixer. The output THz frequency is given by the difference frequency between the two infrared sources. As with the THz TDS method, typically images are acquired on a pixel-by-pixel basis. One of the limitations in applying both the THz TDS and CW photomixing systems to imaging is the requirement for phase coherency between the optical sources that generate and detect the THz radiation.

Over the past few years, a new class of THz imaging method called THz synthetic aperture imaging has emerged. Synthetic aperture imaging methods is usually used in astronomy and radar ranging. Thompson et al., "Interferometry and Synthesis in Radio Astronomy", $2^{nd}$ ed. (Wiley, 2001) p. 50 et seq. THz synthetic aperture imaging methods utilize the THz phase and amplitude measured from multiple positions or from multiple beam paths to reconstruct a THz image. A synthetic aperture THz impulse imaging method which is similar to optical holography has been demonstrated. McClatchey et al., "Time resolved synthetic aperture terahertz impulse imaging," Appl. Phys. Lett. 79, 4485-4487 (2001). For this imaging method, a target is illuminated with pulsed THz and a gated THz receiver records the scattered field. Then a frequency dependent amplitude and phase can be extracted to reconstruct the geometrical shape of the target. Some methods have been developed to solve the inverse problem of image reconstruction using Kirchhoff Migration., Ruffin et al., "Time reversal and object reconstruction with single-cycle pulses", Opt. Lett. 26, 681-683 (2001); Dorney et al., "Terahertz reflection imaging using Kirchhoff migration", Opt. Lett. 26, 1513-1515 (2001).

The foregoing examples of synthetic aperture imaging use a finite number of detectors at specific positions to reconstruct THz images. Synthetic phased array THz imaging methods utilize arrayed optical mirrors to reconstruct field amplitude or energy density, diffraction-limited THz images. J. O'Hara and D. Grischkowsky, "Quasi-optic terahertz imaging", Opt. Lett. 26, 1918-1920 (2001); O'Hara and Grischkowsky, "Synthetic phased-array terahertz imaging", Opt. Lett. 27, 1070-1072 (2002); O'Hara and Grischkowsky, "Quasi-optic synthetic phased-array terahertz imaging," J. Opt. Soc. Am. B 21, 1178-1191 (2004). In these methods several individual images of objects can be recorded. A hybrid system, which combines a high-power electronic source with Ti:sapphire pulsed laser employs heterodyne detection to generate a 2-D reflected-amplitude image through a raster scan by moving the object via an x-y-translation stage. T. Loffler et al., "Continuous-wave terahertz imaging with a hybrid system," Appl. Phys. Lett. 90, 091111 (2007); B. Hils et al., "Terahertz profilometry at 600 GHz with 0.5 um depth resolution," Optics Express. Vol. 16, No. 15 (2008).

SUMMARY OF THE INVENTION

Rather than using a single detector and multiple mirror orientations as in the synthetic phased array approach or using two detectors based on raster-scan imaging, interferometric imaging detects the THz electric field at multiple locations, and then uses the correlated phase and amplitude of the electric field from various pairs of detectors to reconstruct the image. Using the interferometric synthetic aperture imaging method, signals at two or more points in space (the aperture plane at which the detectors of the array are located) are brought together with the proper delay, and correlated both in phase and quadrature to produce cosine and sine components of the brightness distribution. The synthetic aperture imaging methods described herein do not require the source of THz radiation to be phase coherent with the THz detection. Consequently, there is some flexibility in integrating a high power THz source with an independent THz detection array. The present inventors have recently demonstrated video-rate interferometric imaging of a point source using four element detector arrays in which the imaging rate can reach 16 ms per frame. Z. Liu, K. Su, D. Gary, J. Federici, B. Barat, and Z. Michalopoulou, "Video-rate terahertz interferometric and synthetic aperture imaging". Applied Optics vol. 48, No. 19/1 Jul. 2009. According to the methods described therein, the hardware that generates the THz radiation is the same hardware used in the detection process. Consequently, the continuous wave (CW) generation and detection of THz radiation maintains phase coherency.

Unlike the THz video-rate imaging system described above, embodiments of the presently disclosed subject matter do not require the source for CW THz generation and detection to be phase coherent.

In accordance with one embodiment, an imaging system based on heterodyne detection is provided wherein a high-power electronic source is integrated into a CW photomixing detection system.

In one embodiment the present subject matter discloses a THz synthetic aperture imaging system including a continuous wave (CW) photomixing detection apparatus, the CW photomixing apparatus having at least one collimator coupled to a THz detector array, and a first THz radiation source such as one or more lasers for emitting radiation to be received at the at least one collimator; and a second THz radiation source independent of the first THz radiation source, positioned and operable to emit THz radiation toward a sample such that at least some radiation reflected from the sample is received by at least one detector in the THz detector array, wherein the first and second THz radiation sources are phase incoherent.

The system may include an amplifier and antenna operably positioned between the second THz radiation source and a sample. In one embodiment the second THz radiation source is a Gunn Oscillator, operating for example at a frequency of 0.094 THz. The first THz radiation source may be two distributed feedback (DFB) diode lasers operating near 852 nm detuned by 0.094 THz.

In one embodiment the CW photomixing apparatus includes plural beam splitters operably positioned to receive radiation emitted from the first THz radiation source, plural collimators positioned to receive beams from the beam splitters, and optical fibers operably linked to the collimators and the THz detector array. The THz detector array may include at least four THz receivers. The THz detectors may be low-temperature grown GaAs bowtie-type photoconductive dipole antenna (PDA).

In one embodiment the system includes a digitizer and optionally a computer operably linked to the THz detector array. The digitizer includes software or hardware which when executed by a processor causes the processor to digitize data received from the THz detector array.

In a further embodiment the system includes a rotation stage for receiving and rotating a sample.

The presently disclosed imaging system is capable of imaging a THz source at a distance of more than 10 meters, illustrating the potential of the interferometric imaging method for stand-off detection. In addition to improved stand-off imaging distances, the high power THz source enables the demonstration of 2-D THz interferometric imaging of an extended object.

In accordance with another embodiment, methods are disclosed which include obtaining and analyzing the amplitude and phase signals for different pairs of detectors and performing a correlation of each baseline to reconstruct 2D THz images of an extended object with different shapes.

In one embodiment a method is provided which includes illuminating a target with THz radiation from a first THz radiation source, providing a second THz radiation source independent of the first THz radiation source and which is phase incoherent with the first THz radiation source, using the second THz radiation source to provide energy to a continuous wave (CW) photomixing detection apparatus, the CW photomixing apparatus comprising an array of individual THz detectors, detecting a THz electric field using at least one of the detectors in the array of individual THz detectors, obtaining phase and amplitude of the electric field from at least one of the individual THz detectors, correlating phase and amplitude of the electric field, and reconstructing an image of the target using Fourier inversion.

In one embodiment the method includes using at least one pair of detectors to obtain phase and amplitude and calculating the electric field for each of the at least one pair of detectors in the detector array. In another embodiment a method is provided wherein each detector pair correlation provides one spatial Fourier component in a Fourier transform plane comprising U-V data which contains target information, and further includes reconstructing an image of the target through the Fourier inversion using the U-V data of the detector pair combinations.

In another embodiment a method includes illuminating the target with radiation having a frequency of 0.094 THz. One or more methods may include rotating the target around a point of origin.

In another embodiment a method is provided including the step of collecting data from the THz detector array and communicating it to a non-transient, computer readable, storage medium containing a program, which when executed by a processor causes the processor to digitize data received from the THz detector array. At least four detectors may be provided in the THz detector array.

In another embodiment a method includes mixing the frequency of the first THz radiation source, providing two lasers as the second THz radiation source, and varying he difference frequency of the two lasers to tune the CW photomixing detection apparatus to the frequency of the first THz receiver. One method contemplates tuning the frequency of the first THz receiver to 0.094 THz.

BRIEF DESCRIPTION OF THE DRAWINGS

To assist those of ordinary skill in the relevant art in making and using the subject matter hereof, reference is made to the appended drawings, wherein:

FIG. 1A is a graphical depiction of a 4 detector array with spiral configuration in accordance with one embodiment of the present disclosure;

FIG. 1B is a graphical depiction of the 4-detector array in accordance with FIG. 1A showing the corresponding distribution of points in the U-V plane in accordance with one embodiment of the present disclosure;

FIG. 1C is a graphical depiction of the 4-detector array in accordance with FIG. 1B showing the U-V points distribution without symmetry in accordance with one embodiment of the present disclosure;

FIG. 3A is a graphical depiction of a 4 detector array with row configuration after rotation in accordance with one embodiment of the present disclosure;

FIG. 3B is a graphical depiction of the 4-detector array in accordance with FIG. 3A showing the corresponding distribution of points in the U-V plane in accordance with one embodiment of the present disclosure;

FIG. 3C is a graphical depiction of the 4-detector array in accordance with FIG. 3B showing the U-V points distribution without symmetry effect in accordance with one embodiment of the present disclosure;

Figure 2A:
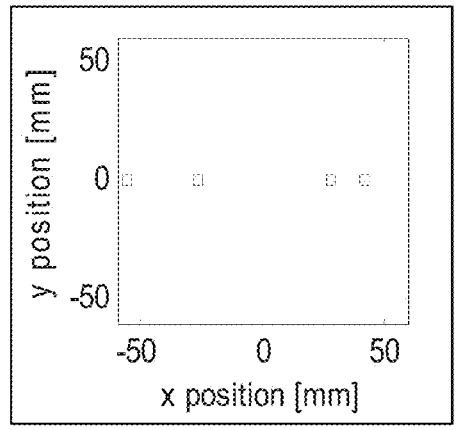
FIG. 2A is a graphical depiction of a 4 detector array with a row configuration in accordance with one embodiment of the present disclosure.

It should be noted that the appended drawings illustrate only typical embodiments of this invention and are therefore not to be construed as limiting of its scope, for the invention may admit to other equally effective embodiments.

DETAILED DESCRIPTION OF THE INVENTION

The following is a detailed description of the invention provided for those skilled in the art of practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Formulae relating to various embodiments of the present invention are described below as they relate to the image quality dependence of the U-V data distribution. For purposes of the following discussion it will be understood by those skilled in the art that an object is illuminated by THz radiation with at least a portion of that radiation reflected toward a THz detector array. For the synthetic aperture imaging methods disclosed herein, the THz electric field is detected simultaneously at multiple locations using the array of individual THz detectors. Correlated phase and amplitude of the electric field are used from various pairs of detectors to reconstruct an image through Fourier inversion. A correlation of the electric field is calculated for each pair of detectors in the detector array. Each detector pair correlation provides one spatial Fourier component in the Fourier transform plane (U-V plane) which contains the target information. Finally the image of the target may be reconstructed through the Fourier inversion using the U-V data of all the different detector pair combinations. Higher image quality may be achieved through a greater number of U-V points. In turn, unlike a focal plane array geometry in which the detectors are evenly spaced, the receivers are spaced within a periodic arrangement, leading to larger coverage of the U-V plane, and consequently more non-redundant Fourier components in the reconstructed images.

The 2-D image is generated through the Fourier inversion:

$$\sigma_E(\xi, \eta) = \sum_{i=1}^{N(N-1)/2} \left[ \begin{array}{l} \text{Re}(A_l e^{i\Delta\phi_l})\cos(k(\mu_l\xi + v_l\eta)) - \\ \text{Im}(A_l e^{i\Delta\phi_l})\sin(k(\mu_l\xi + v_l\eta)) \end{array} \right] \quad [1]$$

where, N is the number of the detectors. There are $N(N+1)/2$ pairs of detectors to be correlated which corresponds $N(N+1)/2$ U-V points in the Fourier transform plan. $\mu_l$ and $v_l$ are baselines between detector pair m and n, which can be expressed as differences of coordinates: $\mu_l = (x_n - x_m)$ and $v_l = (y_n - y_m)$ separately. $A_l$ and $\Delta\phi_l$ are correlated amplitude and phase of the detector pair m and n, which can be expressed as $A_l = E_m E_n$ and $\Delta\phi_l = \phi_m - \phi_n$, respectively. $\xi = x'/Z_0$ and $\eta = y'/Z_0$ are the angular coordinate for point (x', y') on the source surface. $Z_0$ is the distance between the source and detector array.

In experimental results from one embodiment of the present invention, only four receivers are used. Now referring to FIG. 1A, a spiral geometric arrangement of four receivers at the position of (−38.7 mm, 0), (0, −29.27 mm), (32.4 mm, 0), (0, 35.5 mm) is shown. FIGS. 1B and 1C show the corresponding U-V distribution. U-V is spatial frequency, which can be expressed as the spatial distance in wavelength units $$\left(u = \frac{x_n - x_m}{\lambda}, v = \frac{y_n - y_m}{\lambda}\right).$$

There are $N(N+1)/2=6$ (N=4) unique baselines, but there are twice this many points due to symmetry (shown in FIG. 1B). After reducing the symmetry effect, the real U-V sample data distribution is shown in FIG. 1C.

Figure 2B:
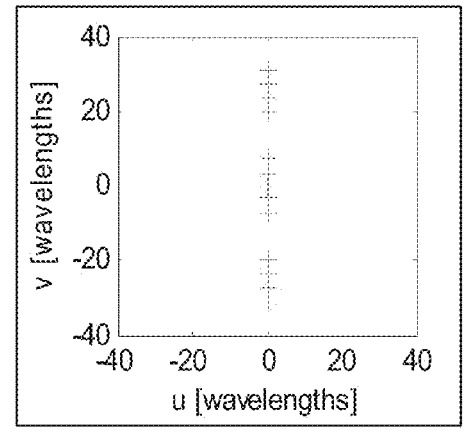
FIG. 2B is a graphical depiction of the 4-detector array in accordance with FIG. 2A showing the corresponding distribution of points in the U-V plane (distance in wavelength) in accordance with one embodiment of the present disclosure.
Figure 2C:
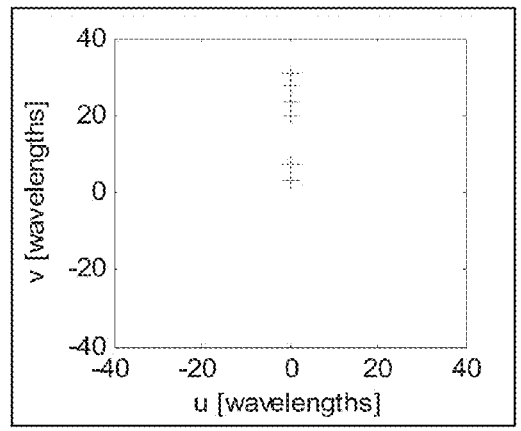
FIG. 2C is a graphical depiction of the 4-detector array in accordance with FIG. 2B showing the U-V points distribution without symmetry in accordance with one embodiment of the present disclosure.

Using this spherical geometric arrangement in accordance with this embodiment, the image of a point source is demonstrated at various distances. Because of the limitation of coverage of U-V plane, only a specific shape of the 2-D image can be generated through this receiver configuration. More U-V data coverage is required for shape-independent object imaging. Thus, in a further embodiment, efficient U-V plane coverage with four detectors may be achieved by rotating the detector array about a fixed axis. Now referring to FIG. 2A, the row geometric arrangement of four individual detector at the positions (−56 mm, 0), (−27 mm, 0), (28 mm, 0) and (42 mm, 0) is depicted. FIG. 2B shows the corresponding distribution of U-V points before rotation. FIG. 2C shows the U-V data distribution after reducing symmetry effect. Now referring to FIGS. 3A-C, after rotating around the receiver center by 10 degree intervals up to 170 degrees, the equivalent number of baselines may be increased from 4 to $18*N(N-1)/2=108(N=4)$, which dramatically improves the quality of the image FIG. 3A shows the detector array with row configuration after rotation. FIG. 3B shows U, V sampling accumulation after 18 rotations. The U, V points are shown twice due to symmetry. FIG. 3C shows the U-V data distribution after reducing symmetry effect.

Figure 4:
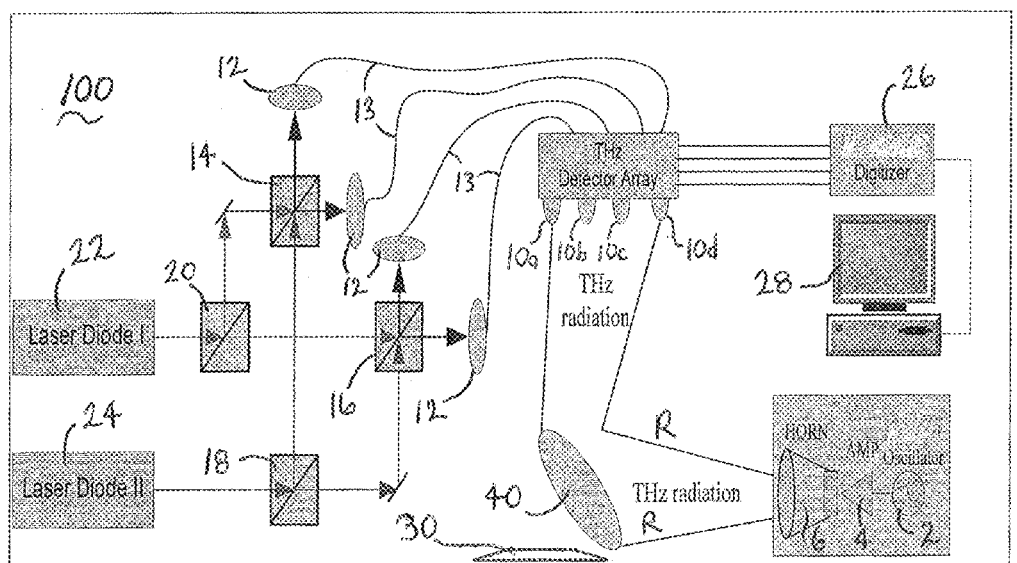
FIG. 4 is a schematic diagram of an incoherent detection THz interferometric imaging system configuration in accordance with one embodiment of the present disclosure.

Now referring to FIG. 4, an experimental set up for one embodiment of an incoherent continuous wave THz interferometric imaging system 100 includes a Thz radiation source 2, amplifier 4, antenna 6, THz detector array 10, collimators 12, fiber optic cables 13, beam splitters 14, 16, 18 and 20, lasers 22 and 24, digitizer 26, computer 28 and rotation stage 30.

The terahertz radiation source 2 is any suitable Thz radiation source, such as a mechanically-tuned Gunn Oscillator (GDM), a voltage-controlled Gunn Oscillator (GDV) or the like. In accordance with one embodiment the THz radiation source is a mechanically-tuned Gunn Oscillator (GDM, Millitech) which is operably linked to a power amplifier 4. Amplifier 4 may be any suitable amplifier such as are commercially available from Millitech of Northampton, Mass. In one embodiment the amplifier 4 is a Millitech AMP amplifier with 8.5 dB gain. In one embodiment the antenna 6 is a horn antenna with output power 50 mW at the operation frequency of 0.094 THz and 354 mw after amplification by the amplifier 4. Thz radiation is emitted by the antenna 6 toward object 40.

Continuous wave (CW) THz radiation is generated at the beating frequency of two distributed feedback (DFB) diode lasers 22, 24 (DL DFB, TOPTICA, DC110) operating near 852 nm. In experimental results relating to one related embodiment of the present invention, the DFB lasers 22, 24 are detuned by 0.094 THz, which is compatible with the GDM source 2. The output of the DFB lasers 22, 24 is evenly split by a first pair of beam splitters 18 and 20, and then combined using a second pair of beam splitters 14 and 16. The combined beam is coupled into polarization-maintaining optical fibers 13 using collimators 12 (such as FiberPort PAF-X-5-A available from ThorLabs) and finally delivered into four THz receivers 10a, 10b, 10c, 10d, respectively. Receivers 10a-10d may be any suitable receivers. In one embodiment the receivers 10a-10d are low-temperature grown GaAs bowtie-type photoconductive dipole antennae (PDA). The optic power of each receiver 10a-10d may be about 20 mw. A bias of ±12V DC may be applied to power the receiver electronics in one exemplary embodiment. It will be apparent to those skilled in the art a greater or lesser number of receivers may be employed.

In one embodiment of the present invention there is no adjustable phase or path length delay in the CW opto-electronic THz detection hardware. The THz source is phase incoherent with respect to the receivers 10a-10d in one embodiment. Also, in one embodiment there is no active frequency locking of the source 2 to the beat frequency of the DFB lasers 22, 24.

In one embodiment a phase coherent PDA THz transmitter may be employed rather than an electronic THz high power source (GDV or GDM, for example). It has been found the high output power of a GDV source dramatically improves the signal-to-noise ratio (SNR).

An object 40 is illuminated by the 0.094 THz radiation R with a portion of that radiation reflected toward the THz detector array 10. In order to increase the numbers of baselines, the object 40 is mounted on the computer-controlled rotation stage 30 and rotated around the origin point by 10 degree intervals up to 170 degrees to simulate the rotation of the detector array 10. Digitizer 26 may be any suitable digitizer. In one embodiment a multichannel digitizer (Micro star Laboratories DAP5400a) is used to collect the data from the four detectors 10-10d simultaneously. The digitizer 26 offers up to 16 channels per board and can acquire 14-bit data at 2M samples per second on each of four channels, which allows for fast speed processing. The digitizer 26 includes a non-transient, computer readable, storage medium containing a program, which when executed by a processor causes the processor to digitize data received from the THz detector array 10. The digitizer may include software which enables display of signals on a GUI such as may be provided in computer 28. The sampling rate may be set to 128 KHz. The amplitude and phase information can be obtained by the Fast Fourier Transform (FFT) onboard digital signal processing capability.

Figure 5A:
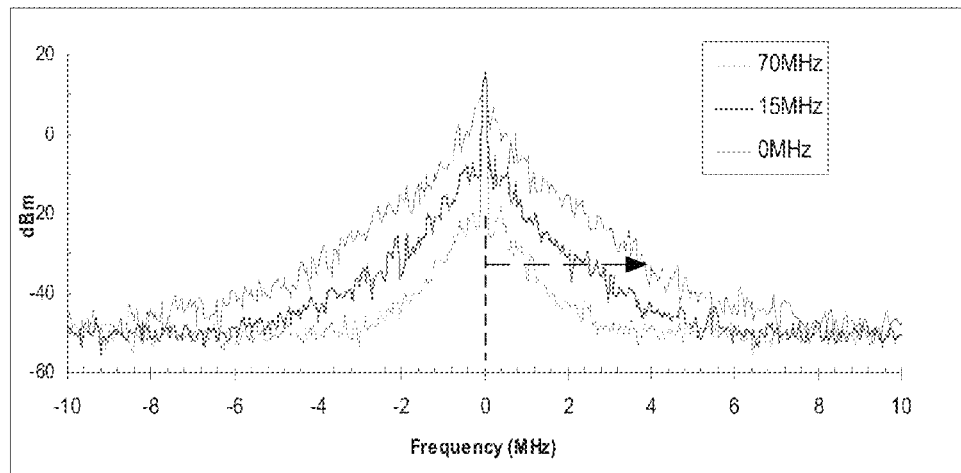
FIG. 5A is a graphical depiction of the spectrum of the PDA receiver with 1 MHz bandwidth at detuning frequencies of 70 MHz, 15 MHz and 0 MHz in accordance with one embodiment of the present disclosure.
Figure 5B:
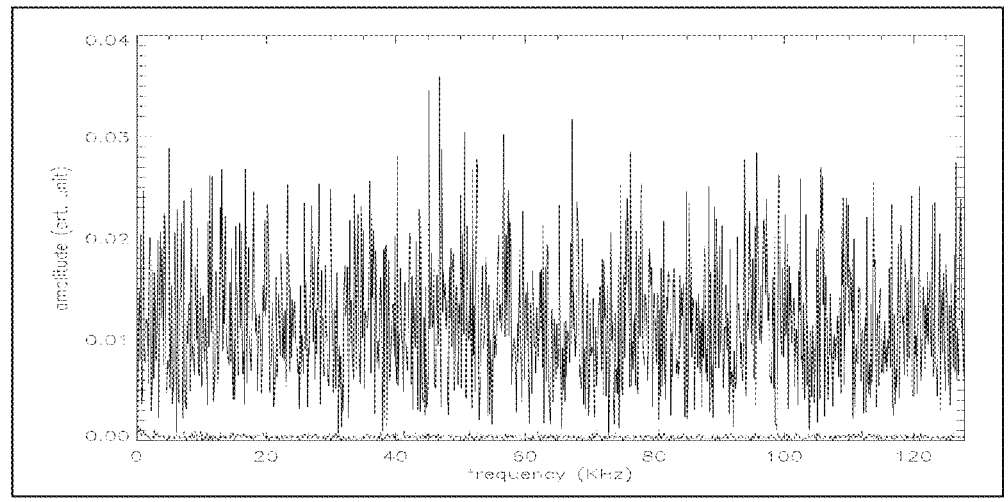
FIG. 5B is a graphical depiction of the frequency spectrum of waveform acquired from the digitizer in accordance with one embodiment of the present disclosure.
Figure 6:
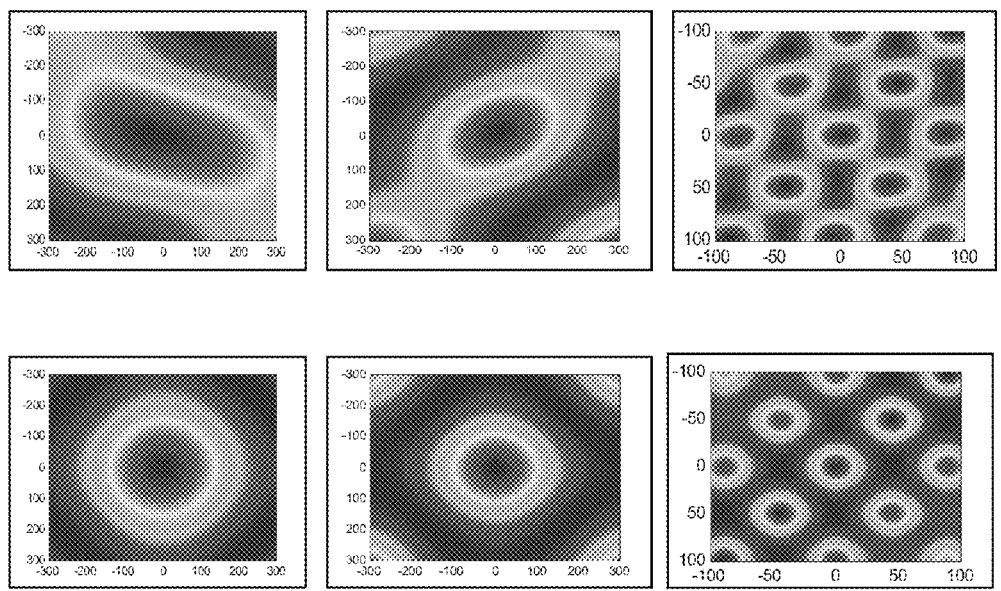
FIG. 6 is a graphical depiction of a comparison of THz imaging of the GDV source (top row) and simulations (bottom row) at the distance of 10.3 meters (left column), 7.6 meters (middle column) and 1 meter (right column) in accordance with one embodiment of the present disclosure.
Figure 7A:
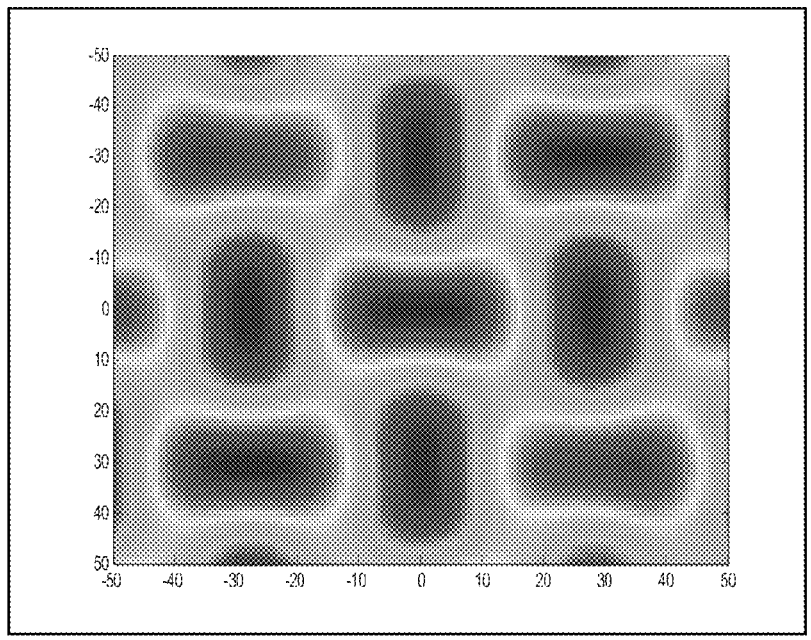
FIGS. 7A and 7B are a graphical depiction of a simulation image of a rectangular shape with limited U-V data in accordance with one embodiment of the present disclosure.
Figure 7B:
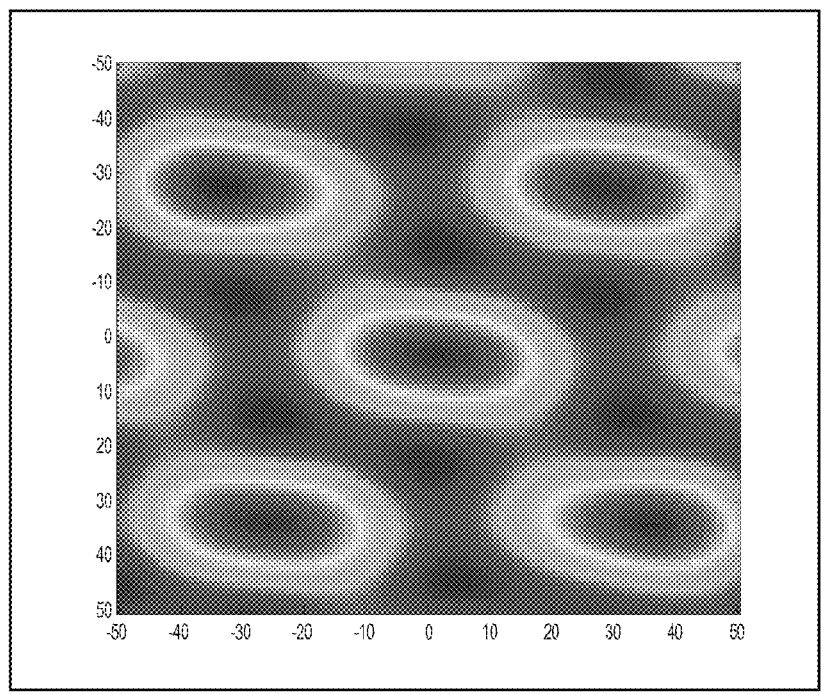
Figure 8A:
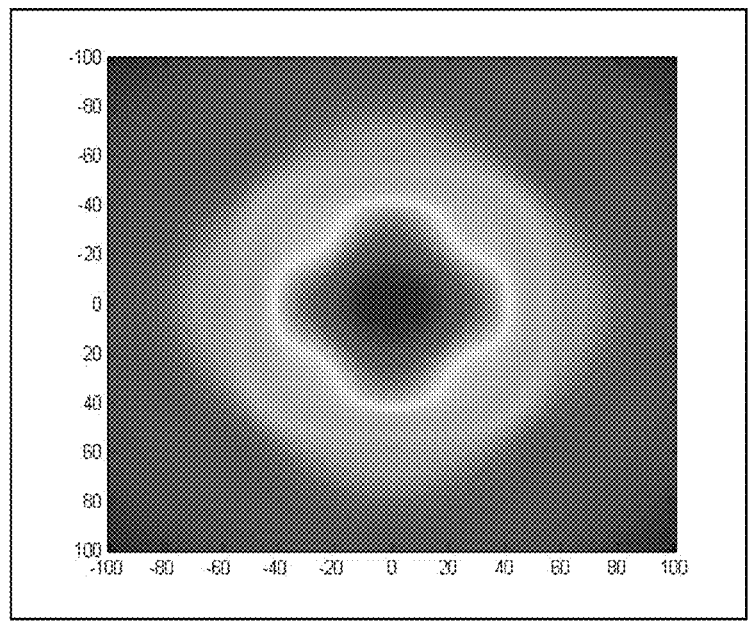
FIG. 8A is a graphical depiction of a simulation image of an object shaped as a cross in accordance with one embodiment of the present disclosure.
Figure 8B:
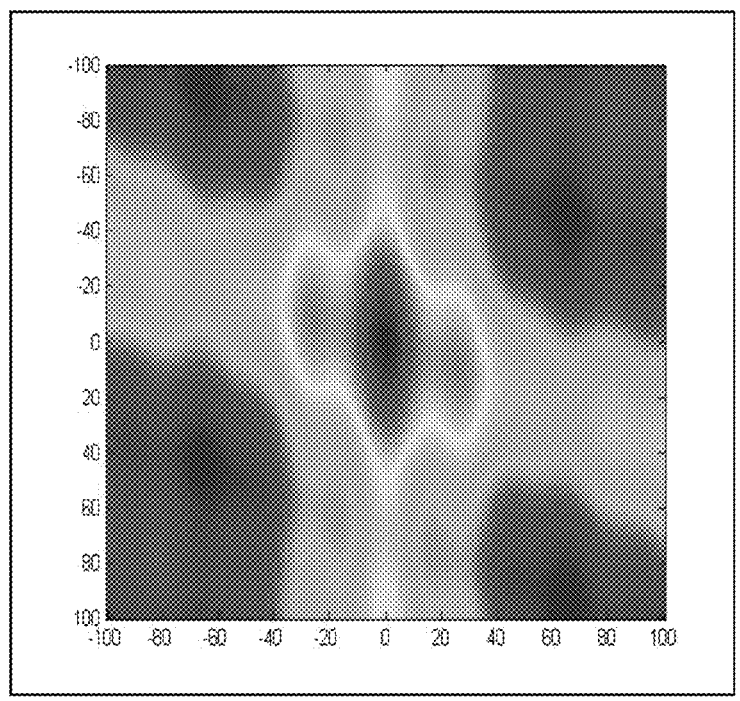
FIG. 8B is a graphical depiction of a Terahertz image reconstructed through experimental data in accordance with one embodiment of the present disclosure. The distortion of the experimental image is caused by the nonuniform response of four receivers and not well defined origin point during rotation.

In order to detect a THz signal, the beat frequency of two DFB lasers 22, 24 should be compatible to the frequency of the Thz radiation source 2, whether it is GDV or GDM or other (0.094 THz). While the Thz radiation source 2 bandwidth is ~20 MHz, the electronic bandwidth of the THz PDA receiver is approximately 1 MHz. The 1 MHz electronic bandwidth corresponds to the intermediate frequency bandwidth of the optical heterodyning THz PDA receiver 10. In one embodiment, the frequency of the Thz radiation source 2 is fixed while the difference frequency of the DFB lasers 22, 24 is varied to tune the CW photomixing receiver to 0.094 THz. As the detection array 10 is tuned to the frequency of the source 2, the detected signal from the PDA within the 1 MHz detection bandwidth increases. Now referring to FIG. 5A, the spectrum of the PDA receiver detected from a digital spectrum analyzer in the digitizer 26 is depicted. Different color lines correspond to the detuning of the source and detection THz frequency. As the beating frequency of the two lasers 22, 24 approaches the frequency of the Thz radiation source 2, the detected signal in the 1 MHz bandwidth increases. For reconstruction of the THz imaging, the output of each detector 10a-10d is digitized. A sample Fourier transform of the digitized waveform from one detector is shown in FIG. 5B. The black, upper line corresponds to the tuning of the source 2 and CW photomixing array to maximum signal while the red, lower line corresponds to a large (>20 MHz) detuning of the source 2 and detection THz frequency.

In the THz video-rate imaging system described in "Video-rate terahertz interferometric and synthetic aperture imaging". Applied Optics vol. 48, No. 19/1 Jul. 2009, incorporated by reference herein in its entirety, a phase modulator which operates at 50 KHz is inserted into the optical path to modulate the phase of the light. In order to reconstruct the image, only one point at 50 KHz in the sample spectrum is collected to achieve the amplitude and phase information for an experiment involving one embodiment of the present invention. However, the imaging system described in multiple embodiments of the present invention does not require the phase modulator. Once the sampling rate is set to 128 KHz, the whole band signal is integrated (including phase and amplitude) and then averaged over whole bandwidth of detector to perform the image reconstruction, which dramatically improves the stability of the correlation phase of the baseline, and hence the stability of the reconstructed image as described herein.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

REFERENCES

J. F. Federici, D. Gary, B. Schulkin. F. Huang. H. Altan, R. Barat, and D. Zimdars, "Terahertz imaging using an interferometric array", Appl. Phys. Lett. 83, 2477 (2003)

A. Bandyopadhyay, A. Stepanov, B. Schulkin, M Federici, A. Sengupta, D. Gary, J. Federici, R. Barat, Z. H. Michalopoulou, D. zimders, "Terahertz interferometric and synthetic aperture imaging" J. Opt. Soc. Amer. A23, 1168 (2006)

K. P. Walsh, B. Schulkin, D. Gary, J. F. Federici, R. Barat, D. Zimdars, "Terahertz near-field interferometric and synthetic aperture imaging" Proc, SPIE 5411, 9 (2004)

A. M. Sinyukov., A. Bandyopadhyay, A. Sengupta, R. B. Barat, D. E. Gary, Z-H. Michalopoulou, Zimdars, and J. F. Federici, "Terahertz interferometric and synthetic aperture imaging," Int. J. High Speed Electron. Syst. 17, 431-443 (2007).

What is claimed is:

1. A Terahertz (THz) interferometric synthetic aperture imaging system comprising a continuous wave (CW) photomixing detection apparatus, the CW photomixing apparatus comprising at least one collimator coupled to a THz detector array, and a first THz radiation source for emitting radiation to be received at the at least one collimator; and a second THz radiation source independent of the first THz radiation source, positioned and operable to emit THz radiation toward a sample such that at least some radiation reflected from the sample is received by at least one detector in the THz detector array, wherein the first and second THz radiation sources are phase incoherent, and wherein the system is operable to detect a THz electric field at multiple locations and use correlated phase and amplitude of the electric field from pairs of detectors to reconstruct an image of the sample.

2. The system according to claim 1 further comprising an amplifier and antenna operably positioned between the second THz radiation source and a sample.

3. The system according to claim 1 wherein the second THz radiation source comprises a Gunn oscillator.

4. The system according to claim 1 wherein the second THz radiation source operates at a frequency of 0.094 THz.

5. The system according to claim 1 wherein the first THz radiation source comprises at least one laser.

6. The system according to claim 5 wherein the first THz radiation source comprises two distributed feedback (DFB) diode lasers operating near 852 nm detuned by 0.094 THz.

7. The system according to claim 1 wherein the CW photomixing apparatus comprises plural beam splitters operably positioned to receive radiation emitted from the first THz radiation source, plural collimators positioned to receive beams from the beam splitters, and optical fibers operably linked to the collimators and the THz detector array.

8. The system according to claim 1 wherein the THz detector array comprises at least four THz receivers.

9. The system according to claim 1 wherein the THz detector array comprises at least one THz detector comprising a low-temperature grown GaAs bowtie-type photoconductive dipole antenna (PDA).

10. The system according to claim 1 further comprising a digitizer and computer operably linked to the THz detector array.

11. The system according to claim 1 comprising a digitizer comprising a non-transient, computer readable, storage medium containing a program, which when executed by a processor causes the processor to digitize data received from the THz detector array.

12. The system according to claim 1 further comprising a rotation stage for receiving a sample.

13. An interferometric synthetic aperture imaging method comprising
    illuminating a target with THz radiation from a first THz radiation source,
    providing a second THz radiation source independent of the first THz radiation source and which is phase incoherent with the first THz radiation source,
    using the second THz radiation source to provide energy to a continuous wave (CW) photomixing detection apparatus, the CW photomixing apparatus comprising an array of individual THz detectors,
    detecting a THz electric field using at least one of the detectors in the array of individual THz detectors,
    obtaining phase and amplitude of the electric field from at least one of the individual THz detectors,
    correlating phase and amplitude of the electric field, and
    reconstructing an image of the target using Fourier inversion.

14. The method according to claim 13 comprising using at least one pair of detectors to obtain phase and amplitude and calculating the electric field for each of the at least one pair of detectors in the detector array.

15. The method according to claim 14 wherein each detector pair correlation provides one spatial Fourier component in a Fourier transform plane comprising U-V data which contains target information, and further comprising reconstructing an image of the target through the Fourier inversion using the U-V data of the detector pair combinations.

16. The method according to claim 13 comprising illuminating the target with radiation having a frequency of 0.094 THz.

17. The method according to claim 13 comprising rotating the target around a point of origin.

18. The method according to claim 13 comprising collecting data from the THz detector array and communicating it to a non-transient, computer readable, storage medium containing a program, which when executed by a processor causes the processor to digitize data received from the THz detector array.

19. The method according to claim 13 comprising providing at least four detectors in the THz detector array.

20. The method according to claim 13, comprising fixing the frequency of the first THz radiation source, providing two lasers as the second THz radiation source, and varying the difference frequency of the two lasers to tune the CW photomixing detection apparatus to the frequency of the first THz source.

21. The method according to claim 20 comprising tuning the frequency of the first THz source to 0.094 THz.

* * * * *